US012661049B2

(12) United States Patent
Zhao et al.

(10) Patent No.: US 12,661,049 B2
(45) Date of Patent: Jun. 23, 2026

(54) FLEXIBLE ELECTRODE AND MANUFACTURING METHOD THEREFOR

(71) Applicant: CENTER FOR EXCELLENCE IN BRAIN SCIENCE AND INTELLIGENCE TECHNOLOGY, CHINESE ACADEMY OF SCIENCES, Shanghai (CN)

(72) Inventors: Zhengtuo Zhao, Shanghai (CN); Xue Li, Shanghai (CN); Chengyao Wang, Shanghai (CN)

(73) Assignee: Center for Excellence in Brain Science and Intelligence Technology, Chinese Academy of Sciences, Shanghai (CN)

( * ) Notice: Subject to any disclaimer, the term of this patent is extended or adjusted under 35 U.S.C. 154(b) by 0 days.

(21) Appl. No.: 18/983,209

(22) Filed: Dec. 16, 2024

(65) Prior Publication Data

US 2025/0134433 A1 May 1, 2025

Related U.S. Application Data

(63) Continuation of application No. PCT/CN2022/102218, filed on Jun. 29, 2022.

(30) Foreign Application Priority Data

Jun. 17, 2022 (CN) .......................... 202210689990.9

(51) Int. Cl.
*A61B 5/25* (2021.01)

(52) U.S. Cl.
CPC .......... *A61B 5/25* (2021.01); *A61B 2562/125* (2013.01); *A61B 2562/164* (2013.01)

(58) Field of Classification Search
CPC ................ A61B 5/25; A61B 2562/125; A61B 2562/164
See application file for complete search history.

(56) References Cited

U.S. PATENT DOCUMENTS

| | | | |
|---|---|---|---|
| 2004/0176831 A1 | 9/2004 | Gliner et al. | |
| 2011/0077660 A1* | 3/2011 | Janik | A61N 1/0553 607/116 |

(Continued)

FOREIGN PATENT DOCUMENTS

| | | |
|---|---|---|
| CN | 101884530 A | 11/2010 |
| CN | 205683398 U | 11/2016 |

(Continued)

OTHER PUBLICATIONS

Huang L, Translation of CN 114469117, May 13, 2022 (Year: 2022).*

(Continued)

*Primary Examiner* — Adam Z Minchella
(74) *Attorney, Agent, or Firm* — COOLEY LLP

(57) ABSTRACT

The present disclosure relates to a flexible electrode and a manufacturing method therefor. Provided is a flexible electrode, comprising at least one implantable and flexible electrode wire and a continuous limiting layer. Each electrode wire comprises: a wire, the wire being located between a first insulating layer and a second insulating layer of the flexible electrode, and an electrode site, the electrode site being in contact with the biological tissue after implantation of the electrode wire, being located on the first insulating layer, and being electrically coupled to the wire by means of a through hole in the first insulating layer. The limiting layer is located on the at least one electrode wire and is configured to be detachably adhered to the at least one electrode wire, (Continued)

so that the at least one electrode wire is kept in a fixed arrangement during the implantation process.

30 Claims, 8 Drawing Sheets

(56)                    References Cited

U.S. PATENT DOCUMENTS

| | | | |
|---|---|---|---|
| 2013/0090542 A1* | 4/2013 | Kipke | A61B 5/685 |
| | | | 607/116 |
| 2015/0151107 A1* | 6/2015 | Schouenborg | A61N 1/05 |
| | | | 604/20 |
| 2017/0311894 A1* | 11/2017 | Nadeau | A61B 5/14539 |
| 2018/0008821 A1* | 1/2018 | Gonzalez | H05K 3/4673 |
| 2020/0085375 A1 | 3/2020 | Tolosa et al. | |
| 2021/0244304 A1 | 8/2021 | Park et al. | |

FOREIGN PATENT DOCUMENTS

| | | | | | |
|---|---|---|---|---|---|
| CN | 106667475 A | | 5/2017 | | |
| CN | 108853717 A | | 11/2018 | | |
| CN | 112993716 A | | 6/2021 | | |
| CN | 113041496 A | | 6/2021 | | |
| CN | 113181549 A | | 7/2021 | | |
| CN | 114080255 A | | 2/2022 | | |
| CN | 114469117 A | * | 5/2022 | ............ | A61B 5/377 |
| JP | 2009285153 A | | 12/2009 | | |
| WO | WO-2021141163 A1 | | 7/2021 | | |
| WO | WO-2023240688 A1 | | 12/2023 | | |

OTHER PUBLICATIONS

International Search Report and Written Opinion (and English translation) for International Application No. PCT/CN2022/102218 mailed Dec. 19, 2022, 14 pages.

* cited by examiner

107

104

102

103

106

101

105

108

100

Manufacturing a flexible separation layer on a substrate — S21

Manufacturing a first insulating layer, a wire layer,
a second insulating layer and an electrode site layer layer
by layer on the flexible separation layer — S22

Removing the flexible separation layer to separate the flexible
electrode from the substrate — S23

200

506
502
504
503
508
501
505
500

FLEXIBLE ELECTRODE AND MANUFACTURING METHOD THEREFOR

CROSS-REFERENCE TO RELATED APPLICATIONS

This application is a continuation of International Application No. PCT/CN2022/102218, filed on Jun. 29, 2022, which claims priority to an application with CN application No. 202210689990.9 filed on Jun. 17, 2022, the disclosures of which are hereby incorporated by reference in their entireties for all purposes.

FIELD OF THE INVENTION

The present disclosure relates to the field of life science technology, and more specifically to a flexible electrode and a manufacturing method therefor.

BACKGROUND OF THE INVENTION

The brain-computer interface (BCI, also known as the brain-machine interface (BMI)) system is a system used to achieve direct signal transmission between the brain and the outside world. It does not rely on traditional pathways composed of the peripheral nervous system to achieve signal acquisition and output, and has broad application prospects in both medical and non-medical fields.

SUMMARY OF THE INVENTION

The following presents a simplified summary of the present disclosure in order to provide a basic understanding of some aspects of the present disclosure. However, it should be understood that this summary is not an exhaustive overview of the present disclosure. It is not intended to identify a key or important part of the present disclosure, nor is it intended to limit the scope of the present disclosure. Its sole purpose is to present some concepts about the present disclosure in a simplified form as a prelude to the more detailed description that is presented later.

According to a first aspect of the present disclosure, provided is a flexible electrode, comprising at least one implantable and flexible electrode wire and a continuous limiting layer, wherein each electrode wire comprises: a wire, the wire being located between a first insulating layer and a second insulating layer of the flexible electrode, and an electrode site, being in contact with the biological tissue after implantation of the electrode wire, located on the second insulating layer, and electrically coupled to the wire by means of a through hole in the second insulating layer; and wherein the limiting layer is located on the at least one electrode wire and detachably adhered to the at least one electrode wire, so that the at least one electrode wire is kept in a fixed arrangement during the implantation process.

According to a second aspect of the present disclosure, provided is a method for manufacturing a flexible electrode, wherein the flexible electrode is the flexible electrode according to the first aspect of the present disclosure, and the method comprises: manufacturing a flexible separation layer on a substrate; manufacturing a first insulating layer, a wire layer, a second insulating layer and an electrode site layer layer-by-layer on the flexible separation layer; and removing the flexible separation layer to separate the flexible electrode from the substrate; wherein before manufacturing the electrode site layer, a through hole is manufactured at a position corresponding to the electrode site in the second insulating layer by patterning.

Other features and advantages of the present disclosure will become more apparent from the following detailed description of exemplary embodiments of the present disclosure with reference to the drawings.

BRIEF DESCRIPTION OF THE DRAWINGS

The drawings, which constitute a part of the specification, illustrate embodiments of the present disclosure and, together with the specification, serve to explain the principles of the present disclosure.

The present disclosure may be more clearly understood from the following detailed description with reference to the drawings, in which.

DETAILED DESCRIPTION OF THE INVENTION

The following detailed description is made with reference to the drawings and is provided to assist in a comprehensive understanding of various exemplary embodiments of the present disclosure. The following description includes various details to assist in understanding but these details are merely exemplary and not for purposes of limiting the present disclosure, which is defined by the appended claims and their equivalents. The words and phrases used in the following description are merely intended to enable a clear and consistent understanding of the present disclosure. In addition, descriptions of well-known structures, functions, and configurations may be omitted for clarity and conciseness. Those of ordinary skill in the art will recognize that various changes and modifications of the examples described herein can be made without departing from the spirit and scope of the present disclosure.

The following description of at least one exemplary embodiment is merely illustrative in nature and is in no way intended to limit the present disclosure, its application, or uses. That is, the structures and methods herein are shown in an exemplary manner to illustrate different embodiments of the structures and methods in the present disclosure. However, those skilled in the art will appreciate that they are merely illustrative of exemplary ways in which the present disclosure may be implemented, and not exhaustive. Furthermore, the drawings are not necessarily drawn to scale, and some features may be enlarged to show details of particular components.

Technologies, methods, and apparatus known to those of ordinary skill in the art may not be discussed in detail, but where appropriate, such technologies, methods, and apparatus should be considered part of the authorization specification.

In all examples shown and discussed herein, any specific values should be interpreted as merely exemplary and not as limiting. Therefore, other examples of the exemplary embodiments may have different values.

Invasive electrode is an important component of brain-machine interface systems, which is in contact with biological tissues such as brain tissue to receive electrical signals from the biological tissues for further processing, or transmits external electrical signals to the biological tissues to, for example, apply stimulation. Invasive electrode needs to be implanted into tissues and keeps in contact with them for a long period of time, so the electrode needs to have relatively good strength, flexibility, stability, biocompatibility, etc. to achieve long-term signal interaction. On the other hand, the electrode needs to transmit as many signals as possible in the smallest possible volume to achieve high-throughput signal interaction while avoiding damage.

Figure 1:
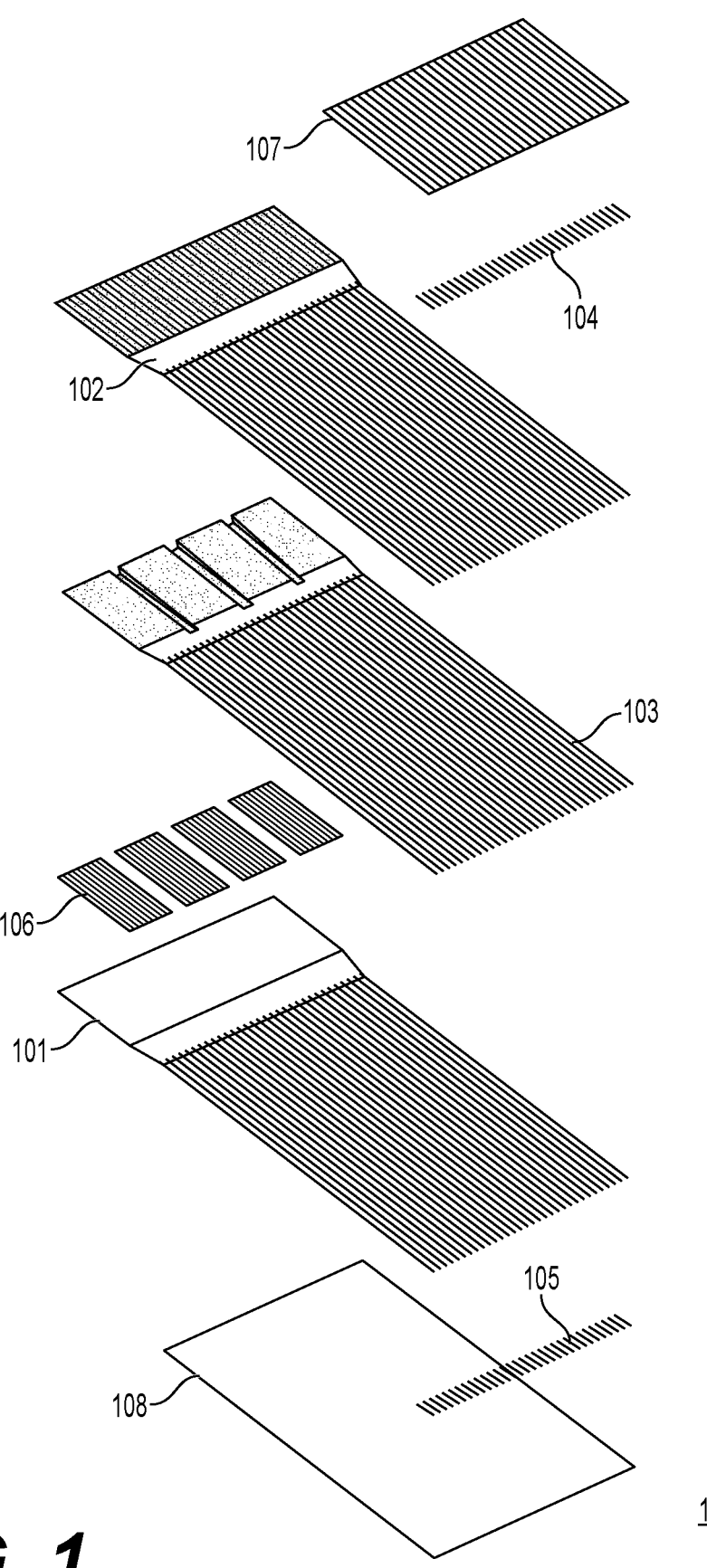
FIG. 1 illustrates an exploded view of at least a portion of a flexible electrode according to an embodiment of the present disclosure.

FIG. 1 illustrates an exploded view of at least a portion of a flexible electrode 100 according to an embodiment of the present disclosure.

It can be clearly seen from FIG. 1 that the flexible electrode 100 is a multi-layer structure, specifically, comprising a bottom insulating layer 101, a top insulating layer 102, a wire layer 103, a top electrode site layer 104, a bottom electrode site layer 105, a back end site layer 106, a limiting layer 107, a flexible separation layer 108, etc. It should be understood that the various layers of the flexible electrode 100 shown in FIG. 1 are merely non-limiting examples, and the flexible electrode in the present disclosure may omit one or more of the layers, or may comprise more other layers.

As shown in FIG. 1, the flexible electrode 100 may comprise a back end portion and a plurality of flexible electrode wires each extending from the back end portion, all of which have a multilayer structure, wherein the back end portion may be configured to join the electrode wires and back end circuits for back end switching, and the flexible electrode wires have good flexibility and may be partially or fully implanted into a biological tissue to collect electrical signals from or apply electrical signals to the biological tissue. The flexible electrode 100 shown in FIG. 1 comprises a plurality of flexible electrode wires. However, it should be understood that the flexible electrode in the present disclosure may comprise one or more electrode wires. For example, referring to FIGS. 4 and 5, the flexible electrode 400 and the flexible electrode 500 shown both comprise a single flexible electrode wire extending from a back end portion. These electrode wires may have a width and thickness of nanometer or micrometer scale, and a length that is several orders of magnitude greater than the width and thickness (such as, of centimeter scale) as required. In an embodiment according to the present disclosure, the thickness and width of the electrode wire may range from 100 nm to 200 μm. It should be understood that the shape, size, etc. of the electrode wire are not limited to the ranges listed above, but can be changed according to design requirements.

Specifically, the flexible electrode 100 may comprise an insulating layer 101 located at the bottom of the electrode and an insulating layer 102 located at the top of the electrode. The insulating layer in the flexible electrode may refer to an outer surface layer of the electrode that plays an insulating role. Since the insulating layer of the flexible electrode needs to be in contact with a biological tissue after implantation, the material of the insulating layer is required to have both good insulativity and good biocompatibility. In an embodiment of the present disclosure, the material of the insulating layers 101 and 102 may include polyimide (PI), polydimethylsiloxane (PDMS), parylene, epoxy resin, poly-amideimide (PAI), and the like. In addition, the insulating layers 101 and 102 are also the main parts of the flexible electrode 100 that provide strength. If the insulating layer is too thin, the strength of the electrode will be reduced, and if the insulating layer is too thick, the flexibility of the electrode will be reduced. In addition, implantation of an electrode comprising an insulating layer that is too thick will cause greater damage to the organism. In an embodiment according to the present disclosure, the thickness of the insulating layers 101, 102 may be 100 nm to 300 μm, preferably 300 nm to 3 μm, more preferably 1 μm to 2 μm, 500 nm to 1 μm, etc.

Each flexible electrode wire in the flexible electrode 100 may comprise wires in a wire layer 103 between the bottom insulating layer 101 and the top insulating layer 102. In an embodiment according to the present disclosure, each flexible electrode wire may comprise one or more wires in the same wire layer 103. For example, it can be clearly seen from FIG. 7 that the wire layer 703 of the flexible electrode wire 700 comprises a plurality of wires, wherein each wire comprises an elongated main body portion and an arcuate end portion corresponding to a corresponding electrode site. The spacing between the wires can be as low as 10 nm, for example. The width of the wires and the spacing between the wires may be, for example, 10 nm to 500 μm, for example, preferably 100 nm to 3 μm. It should be understood that the shape, size, spacing etc. of the wires are not limited to the ranges listed above, but can be changed according to design requirements.

In an embodiment according to the present disclosure, the wires in the wire layer 103 may be a film structure comprising a plurality of layers stacked in the thickness direction. These layered materials may be materials that enhance the properties of the wire such as adhesion, ductility, and conductivity. As a non-limiting example, the wire layer 103 can be a metal film comprising three stacked layers, wherein the first layer and the second layer in contact with the insulating layers 101 and 102 respectively are made of metal adhesive materials such as titanium (Ti), titanium nitride (TIN), chromium (Cr), tantalum (Ta) or tantalum nitride (TaN), or non-metal adhesive materials, and the third layer located between the first layer and the second layer is made of a material with good conductivity such as gold (Au), platinum (Pt), iridium (Ir), tungsten (W), magnesium (Mg), molybdenum (Mo), platinum-iridium alloy, titanium alloy, graphite, carbon nanotubes, PEDOT. It should be understood that the wire layer may also be made of other conductive metal materials or non-metal materials, or may be made of polymer conductive materials and composite conductive materials.

The flexible electrode wire may further comprise electrode sites in a top electrode site layer 104 located on the top insulating layer 102, and these electrode sites may be in contact with biological tissues after the flexible electrode is implanted to directly collect or apply electrical signals. In the flexible electrode 100, the electrode sites in the top electrode site layer 104 may be electrically coupled to corresponding wires by means of through holes in the top insulating layer 102 at positions corresponding to the electrode sites. In the case where the flexible electrode wire comprises a plurality of wires, the flexible electrode wire may accordingly comprise a plurality of electrode sites in the top electrode site layer 104, and each of the electrode sites is electrically coupled to one of the plurality of wires through a corresponding through hole in the top insulating layer 102. For example, still referring to FIG. 7, for the electrode wire 700 in FIG. 7, each electrode site 704 may have a corresponding wire in the wire layer 703. Each electrode site may have a microscale planar dimension and a nanoscale thickness. In an embodiment according to the present disclosure, the electrode sites may comprise sites with a diameter of 1 μm to 500 μm, and the spacing between the electrode sites may be 1 μm to 5 mm. In an embodiment according to the present disclosure, the electrode sites may be in the shape of a circle, an ellipse, a rectangle, a rounded rectangle, a chamfered rectangle, or the like. It should be understood that the shape, size, spacing, etc. of the electrode sites can be selected according to the conditions of the biological tissue area to be recorded or stimulated.

In an embodiment according to the present disclosure, the electrode sites in the top electrode site layer 104 may be a film structure comprising a plurality of layers stacked in the thickness direction. The material of the layer close to the wire layer 103 among the plurality of layers may be a material that can enhance adhesion between the electrode site and the wire. As a non-limiting example, the electrode site layer 104 may be a metal film comprising two stacked layers, wherein the first layer close to the wire layer 103 is Ti, TiN, Cr, Ta or TaN, and the second layer of the electrode site layer 104 exposed to the outside is Au. It should be understood that the electrode site layer can, similar to the wire layer, be made of other conductive metal materials or non-metallic materials, such as Pt, Ir, W, Mg, Mo, platinum-iridium alloy, titanium alloy, graphite, carbon nanotubes, PEDOT.

In an embodiment according to the present disclosure, the surface of the electrode site that is exposed to the outside and in contact with the biological tissue may also have a surface modification layer to improve the electrochemical properties of the electrode site. As a non-limiting example, the surface modification layer can be obtained by utilizing methods such as an electro-induced polymerization coating of PEDOT: PSS, a sputtered iridium oxide film. It is used to reduce impedance (such as electrochemical impedance at an operating frequency of 1 kHz) when the flexible electrode collects electrical signals, and to improve charge injection capability when the flexible electrode applies electrical signal stimulation, thereby improving the interaction efficiency.

In an embodiment according to the present disclosure, the flexible electrode wire may further comprise electrode sites in a bottom electrode site layer 105 located under the bottom insulating layer 101, and the electrode sites may be in contact with biological tissues after the flexible electrode is implanted to directly collect or apply electrical signals. Similar to the electrode sites in the top electrode site layer 104, in the flexible electrode 100, the electrode sites in the bottom electrode site layer 105 may be electrically coupled to corresponding wires by means of through holes at positions corresponding to the electrode sites in the bottom insulating layer 101. In an embodiment according to the present disclosure, the electrode sites in the bottom electrode site layer 105 and the electrode sites in the top electrode site layer 104 may be located at opposite positions on the top and bottom sides of the flexible electrode 100, and the electrode sites in the bottom electrode site layer 105 and the electrode sites in the top electrode site layer 104 located at opposite positions are electrically coupled to the same wire in the wire layer 103. In an embodiment according to the present disclosure, the electrode sites in the bottom electrode site layer 105 and the electrode sites in the top electrode site layer 104 may also be located at different positions on the top and bottom sides of the flexible electrode 100 to collect or apply electrical signals in different areas of biological tissues; and in an embodiment according to the present disclosure, the electrode sites in the bottom electrode site layer 105 may also be electrically coupled to a wire in the wire layer 103 that is different from that for the electrode sites in the top electrode site layer 104.

It should be understood that the bottom electrode site layer 105 is an optional but not necessary portion of the flexible electrode. For example, the flexible electrode in the present disclosure may only comprise the top electrode site layer 104 but not the bottom electrode site layer 105. The shape, size, material, etc. of the bottom electrode site may be similar to those of the top electrode site and will not be described in detail here.

In an embodiment of the present disclosure, the flexible electrode may further comprise an additional wire layer, that is, the flexible electrode in the present disclosure may comprise one or more wire layers. The size, material, manufacturing method, etc. of the additional wire layer may be similar to those of the wire layer 103 and will not be described in detail herein. In the case where the flexible electrode comprises additional wire layers, these wire layers may be separated by additional insulating layers. The size, material, and manufacturing method of the additional insulating layers may be similar to those of the bottom insulating layer 101 and/or the top insulating layer 102, and will not be described in detail here. One or more of the wires in these additional wire layers may be electrically coupled to electrode sites located under the bottom insulating layer or above the top insulating layer by means of through holes in one or more of the bottom insulating layer, the top insulating layer, or the additional insulating layer. By comprising a plurality of wire layers in the flexible electrode, the number and accuracy of signals transmitted through the flexible electrode can be increased with the same cross-sectional width, that is, a high-precision and multi-channel electrode is provided, which is conducive to achieving high-throughput interaction.

In an embodiment according to the present disclosure, the back end portion of the flexible electrode 100 may comprise a back end site in a back end site layer 106. The back end site can be electrically coupled to one of the wires and electrically coupled to a back end circuit by means of a through hole in the bottom insulating layer 101 and/or the top insulating layer 102 to achieve bidirectional signal transmission between the electrode site electrically coupled to the wire and the back end circuit. Here, the back end circuit may refer to a circuit at the back end of the flexible electrode, such as a recording circuit, a processing circuit associated with the signal of the flexible electrode. In an embodiment according to the present disclosure, the flexible electrode can be connectively coupled to the back end circuit. Specifically, the ball gate array (BGA) packaging site as the back end site can be switched to a commercial signal recording system through a printed circuit board (PCB), a flexible printed circuit (FPC), etc. The connection methods include bumping and anisotropic conductive film bonding (ACF Bonding), etc. In an embodiment according to the present disclosure, the flexible electrode can also be integrated with the back end circuit. Specifically, pre-processing functions such as signal amplification and filtering can be integrated on a dedicated chip, and then connected and packaged with an integrated PCB at the back end of the flexible electrode through bonding or the like, thereby realizing wireless transmission and charging, etc. In this case, an independent flexible electrode and an independent dedicated chip as the back end circuit can be used, and the electrical connection between the flexible electrode and the dedicated chip can be made through bumping or ACF Bonding. Alternatively, a certain space can be reserved on the pre-tapeout wafer of the chip serving as the back end circuit, and the electrode can be directly manufactured on this basis, thereby realizing the joint processing or separate processing technology of the chip and the electrode to achieve a higher level of integration.

The back end site may have a microscale planar dimension and a nanoscale thickness. As a non-limiting example, the back end site may be a BGA packaging site with a diameter of 50 μm to 2000 μm, or may be a circular, oval, rectangular, rounded rectangular, chamfered rectangular site with a side length of 50 μm to 2000 μm. It should be understood that the shape, size, etc. of the back end site are not limited to the ranges listed above, but can be changed according to design requirements.

The back end site in a connected manner may comprise a plurality of layers in the thickness direction, the material of the adhesive layer close to the wire layer 103 among the plurality of layers may be a material that can enhance the adhesion between the electrode site and the wire, the material of the middle flux layer among the plurality of layers may be a flux material, the conductive layer among the plurality of layers may, like the wire layer described above, use other conductive metal materials or non-metallic materials, and the outermost layer among the plurality of layers that may be exposed through the insulating layers 101 and 102 is an anti-oxidation protective layer. As a non-limiting example, the back end site layer 106 can be a metal film comprising three stacked layers, wherein the first layer close to the wire layer 103 can be a nanoscale adhesive layer to improve the adhesion between the back end site layer 106 and the wire layer 103, the second layer as a flux layer can be nickel (Ni), Pt or palladium (Pd), and the third layer as a conductive layer can be Au, Pt, Ir, W, Mg, Mo, platinum-iridium alloy, titanium alloy, graphite, carbon nanotubes, PEDOT, etc. It should be understood that the back end site layer may also be made of other conductive metal materials or non-metal materials. The back end site layer 106 in FIG. 1 is the part connected to the back end processing system or chip. The size, spacing, shape, etc. of the sites can be redesigned according to different back end connections. FIG. 1 shows the sites of a 512-channel electrode, including 4 128 BGAs. It should be understood that electrode sites with other numbers of channels may be included as needed, such as 32, 36, 64, 128 channels.

In an embodiment according to the present disclosure, the flexible electrode may not comprise site layers such as a top electrode site layer, a bottom electrode site layer, a back end site layer. In this case, the electrode sites on the electrode wire and the back end sites in the back end portion for switching may both be portions in the wire layer and electrically coupled to the corresponding wires in the wire layer. Furthermore, the electrode sites for sensing and applying electrical signals can be directly in contact with the tissue area into which the electrode wire is implanted. As a non-limiting example, each electrode site can be electrically coupled to a corresponding wire in the wire layer, and exposed to the outer surface of the electrode wire and in contact with the biological tissue through a corresponding through hole in the top insulating layer or the bottom insulating layer.

In an embodiment according to the present disclosure, the flexible electrode 100 may further comprise a continuous limiting layer 107. As shown in FIG. 1, the limiting layer 107 may be located on the electrode wires and detachably adhered to the electrode wires (e.g., by bonding forces such as van der Waals forces) such that the electrode wires are kept in a fixed arrangement after being separated from the substrate. The limiting layer 107 can be manufactured to enable the separation of the flexible electrode wire from the limiting layer 107 without damaging the flexible electrode wire. Also, based on the limiting layer 107, it can easily identify the flexible electrode wire to be implanted and the relative position of the flexible electrode wire from the plurality of electrode wires of the flexible electrode 100, thereby creating conditions for the realization of automatic implantation. In an embodiment of the present disclosure, the material of the limiting layer can be parylene, but it should be understood that any other alternative material that meets the limiting and separable characteristics can also be used as the material of the limiting layer, such as PDMS, UV film, low-viscosity and residue-free electronic-grade tapes such as blue film can also be used, and plastic films with heat shrink properties can be used.

In an embodiment according to the present disclosure, a separation layer may exist between the limiting layer 107 and the top electrode site layer 104, and the outermost layer among the plurality of layers of the top electrode site layer 104 may adopt the same material as the flexible separation layer, such as Ni. For example, the top electrode site layer 104 may be a metal film composed of three layers of Ti, Au, and Ni. In addition, in an embodiment according to the present disclosure, the limiting layer 107 may also have limiting layer holes at positions corresponding to the electrode sites in the top electrode site layer 104, and the contour of the limiting layer holes may be surrounded by the contour of the corresponding electrode sites. Thus, in this case, separation between the limiting layer 107 and the top electrode site is achieved without damaging the electrode site.

In an embodiment according to the present disclosure, the flexible electrode 100 may further comprise a flexible separation layer 108. The flexible separation layer 108 of the flexible electrode 100 in FIG. 1 is shown as being located at the bottom of the entire flexible electrode, but it should be understood that the position of the flexible separation layer is not limited thereto, and the flexible electrode may comprise one or more flexible separation layers located at different positions. For example, as described above, a flexible separation layer may preferably be manufactured between the limiting layer and the top electrode site layer. The flexible separation layer may be made of a material that can be removed by a specific substance (such as a solution) to separate the two portions of the flexible electrode above and below the flexible separation layer while avoiding damage to the flexible electrode. Specifically, the flexible separation layer can be used to separate the entire electrode or only the flexible portion of the electrode from the substrate, to separate a flexible substrate from a hard substrate, to separate portions that have too strong adhesion but need to be separated, etc. In an embodiment of the present disclosure, the material of the flexible separation layer may be a metal such as Ni, Cr, aluminum (Al), or a non-metal material.

Figure 2:
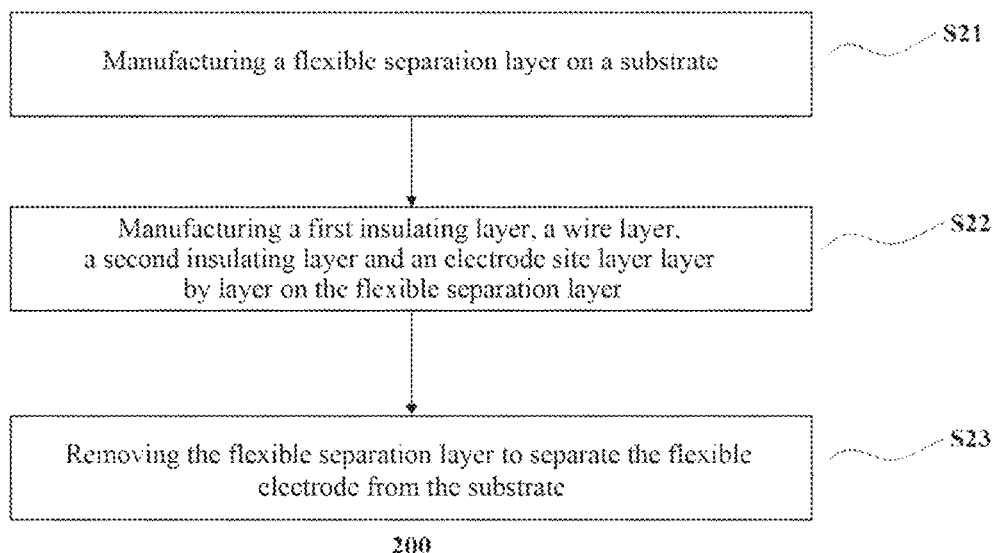
FIG. 2 shows a flow chart of a method for manufacturing a flexible electrode according to an embodiment of the present disclosure.

FIG. 2 shows a flow chart of a method 200 for manufacturing a flexible electrode according to an embodiment of the present disclosure. In the present disclosure, nanoscale flexible electrodes can be manufactured by using a manufacturing method based on a micro-electro mechanical system (MEMS) process. As shown in FIG. 2, method 200 may comprise: at S21, manufacturing a flexible separation layer on a substrate; at S22, manufacturing a first insulating layer, a wire layer, a second insulating layer and an electrode site layer layer-by-layer on the flexible separation layer, wherein before manufacturing the electrode sites, through holes are manufactured at positions corresponding to the electrode sites in the first insulating layer by patterning; and at S23, removing the flexible separation layer to separate the flexible electrode from the substrate.

Figure 3:
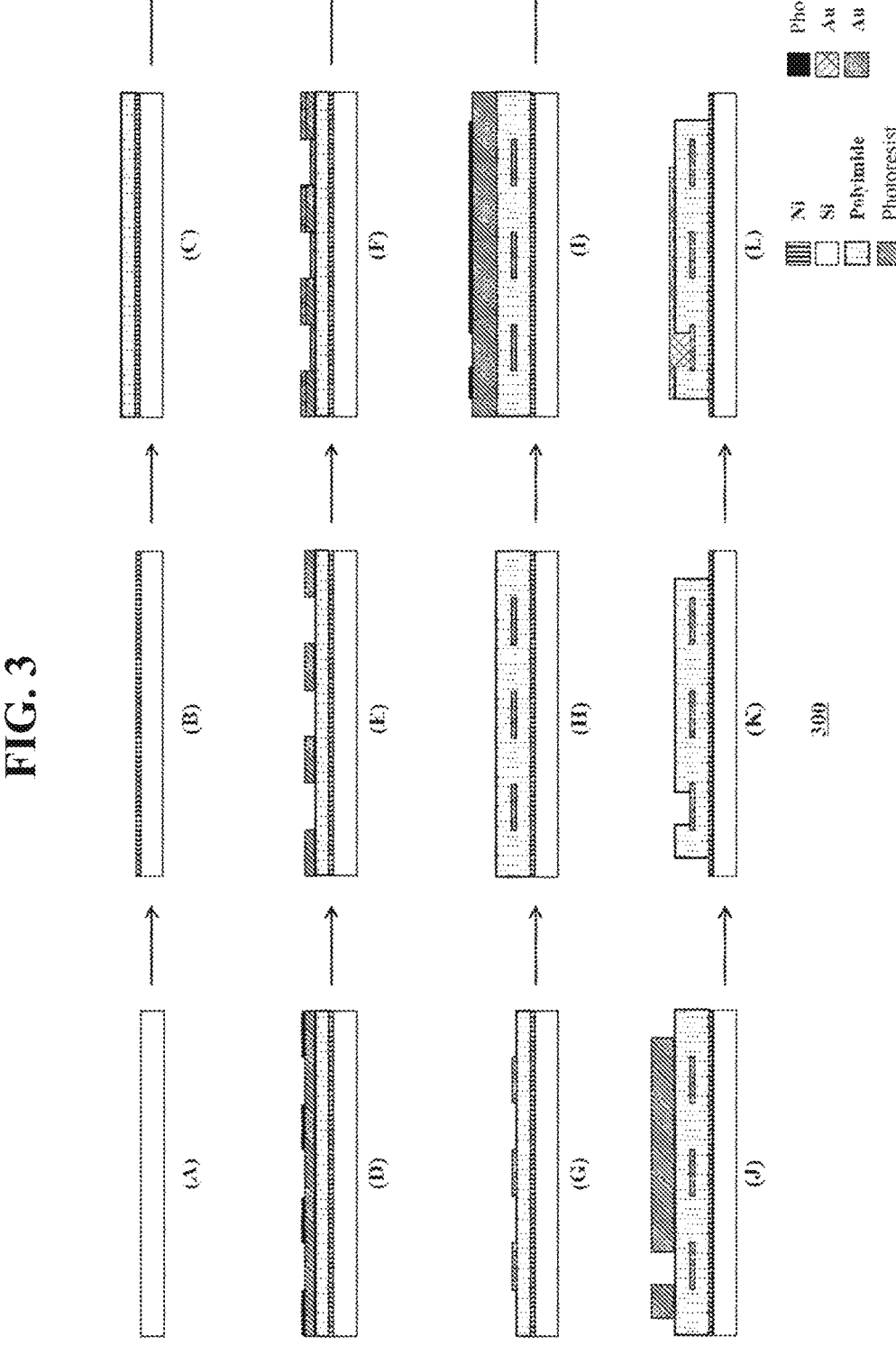
FIG. 3 shows a schematic diagram of a method for manufacturing a flexible electrode according to an embodiment of the present disclosure.

FIG. 3 shows a schematic diagram of a method 300 for manufacturing a flexible electrode according to an embodiment of the present disclosure. The manufacturing process and structure of the flexible separation layer, the bottom insulating layer, the wire layer, the top insulating layer, the electrode site layer and other portions of the flexible electrode are described in more detail in conjunction with FIG. 3.

View (A) of FIG. 3 shows the substrate of the electrode. In an embodiment according to the present disclosure, a hard substrate such as glass, quartz, silicon wafer, etc. may be used. In an embodiment of the present disclosure, other soft materials may also be used as the substrate, such as the same material as the insulating layer.

View (B) of FIG. 3 shows the step of manufacturing a flexible separation layer on a substrate. The flexible separation layer can be removed by applying specific substances, thus facilitating the separation of the flexible portion of the electrode from the hard substrate. The embodiment shown in FIG. 3 uses Ni as the material of the flexible separation layer, and other materials such as Cr and Al may also be used. In an embodiment according to the present disclosure, when a flexible separation layer is manufactured on a substrate by evaporation, a portion of the substrate exposed may be etched first, thereby improving the flatness of the entire substrate after evaporation. It should be understood that the flexible separation layer is an optional and not a necessary portion of the flexible electrode. Depending on the properties of the selected materials, the flexible electrode can also be conveniently separated without a flexible separation layer. In an embodiment according to the present disclosure, the flexible separation layer may further have a mark, which may be used for alignment of subsequent layers.

View (C) of FIG. 3 shows the manufacturing of a bottom insulating layer on the flexible separation layer. As a non-limiting example, in the case where the insulating layer is made of polyimide material, the manufacturing of the bottom insulating layer may comprise steps such as film forming process, film curing and enhanced curing to manufacture a film as the insulating layer. The film forming process may comprise coating polyimide on the flexible separation layer, such as by spin coating a layer of polyimide at a segmented rotational speed. Film curing may comprise gradually increasing the temperature to a higher temperature and maintaining the temperature to form a film, thereby performing subsequent processing steps. Enhanced curing may comprise, before manufacturing subsequent layers, multi-gradient temperature rising, preferably in a vacuum or nitrogen atmosphere, and baking for several hours. It should be understood that the above manufacturing process is only a non-limiting example of the manufacturing process of the bottom insulating layer, and one or more steps may be omitted, or more other steps may be comprised.

It should be noted that the above manufacturing process is directed to an embodiment of manufacturing a bottom insulating layer in a flexible electrode without a bottom electrode site layer and without through holes corresponding to the electrode sites in the bottom insulating layer. If the flexible electrode comprises a bottom electrode site layer, the bottom electrode site layer may be manufactured on the flexible separation layer before manufacturing the bottom insulating layer. For example, Au and Ti may be sequentially evaporated on the flexible separation layer. The patterning steps for the bottom electrode sites will be described in detail later with respect to the top electrode sites. Accordingly, in the case where the flexible electrode comprises a bottom electrode site, in the process of manufacturing the bottom insulating layer, in addition to the above steps, a patterning step may be comprised for etching a through hole at a position in the bottom insulating layer corresponding to the bottom electrode site. The patterning step of the insulating layer will be described in detail later with respect to the top insulating layer.

Views (D) to (G) of FIG. 3 show the manufacturing of a wire layer on the bottom insulating layer. As shown in View (D), a photoresist and a photomask may be applied on the bottom insulating layer. It should be understood that other photolithographic means may also be used to prepare patterned films, such as laser direct writing and electron beam lithography. In an embodiment according to the present disclosure, for a metal film such as a wire layer, a double layer of photoresist may be applied to facilitate the manufacturing (evaporation or sputtering) and peeling of the patterned film. By setting the pattern of the photomask associated with the wire layer, for example, the pattern of the wire layer 103 shown in FIG. 1, i.e., the contour of one or more wires in each electrode wire extending from the back end portion, can be achieved. Then, exposure and development may be performed to obtain a structure as shown in View (E). In an embodiment according to the present disclosure, exposure may be performed by contact lithography, where the mask and the structure are exposed in a vacuum contact mode. In an embodiment according to the present disclosure, different developers with different concentrations may be used for patterns of different sizes. In an embodiment according to the present disclosure, if the structure is large and the amount of developer is small, in order to prevent insufficient development causing photoresist residue and thus causing the patterned film to fall off during stripping, a photoresist removing process may be performed after development. This step may also comprise aligning the layers. Next, a film may be formed on the structure shown in View (E), for example, by using a process such as evaporation or sputtering to deposit a metal film material, such as Au, to obtain a structure shown in View (F). Next, stripping may be performed to separate the film in the non-patterned area from the film in the patterned area by removing the photoresist in the non-patterned area, thereby obtaining a structure as shown in View (G), that is, manufacturing a wire layer.

In an embodiment according to the present disclosure, before manufacturing the wire layer, a back end site layer may also be manufactured. As a non-limiting example, the manufacturing process of the back end site layer can be similar to the manufacturing process of the metal film described above with respect to the wire layer.

Views (H) to (K) of FIG. 3 illustrate the manufacturing of the top insulating layer. For photosensitive films, patterning can generally be achieved directly through patterned exposure and development, while for non-photosensitive materials used in insulating layers, patterning cannot be achieved by exposing and developing themselves. Therefore, a sufficiently thick patterned anti-etching layer can be manufactured on this layer, then the film in the area not covered by the anti-etching layer can be removed by dry etching (the anti-etching layer will also become thinner, so the anti-etching layer must be thick enough), and then the anti-etching layer can be removed to achieve patterning of the non-photosensitive layer. As a non-limiting example, the insulating layer may be manufactured using a photoresist as the anti-etching layer. The manufacturing of the top insulating layer may comprise the steps of film forming process, film curing, patterning, enhanced curing, etc., wherein View (H) shows the structure obtained after the top insulating layer is formed, View (I) shows the application of photoresist and photomask on the top insulating layer after film forming, View (J) shows the structure of the anti-etching layer obtained after exposure and development, and View (K) shows the structure of the prepared top insulating layer. The film forming process, film curing and enhanced curing have been described in detail in the above description regarding the bottom insulating layer, and are omitted here for the sake of brevity. The patterning step can be performed after film curing, or after enhanced curing. After enhanced curing, the insulating layer has a stronger etching resistance. Specifically, in View (I), a sufficiently thick photoresist layer is manufactured on the insulating layer through steps such as spin coating and baking. By setting the pattern of the photomask related to the top insulating layer, for example, the pattern of the top insulating layer 102 shown in FIG. 1 can be achieved, that is, the contour of the top insulating layer achieved on one or more wires of each electrode wire extending from the back end portion and the contour of the through hole achieved at the position corresponding to the electrode site in the top insulating layer. In View (J), the pattern is transferred to the photoresist on the insulating layer through exposure, development and other steps to obtain an anti-etching layer, wherein the portion to be removed from the top insulating layer is exposed. The exposed portion of the top insulating layer may be removed by oxygen plasma etching to obtain the structure shown in View (K).

In an embodiment according to the present disclosure, the top insulating layer may be subjected to an adhesion enhancement treatment before being manufactured to improve the bonding force between the bottom insulating layer and the top insulating layer.

View (L) of FIG. 3 shows manufacturing of a top electrode site layer on the top insulating layer.

In an embodiment according to the present disclosure, a limiting layer may also be manufactured on the top electrode site layer. Similar to the insulating layer, the material of the limiting layer can be a non-photosensitive material. Therefore, in order to manufacture limiting layer holes in the limiting layer, for example, the step of patterning the limiting layer can be achieved by manufacturing an anti-etching layer, etching away the film in the area not covered by the anti-etching layer, and then removing the anti-etching layer. In an embodiment of the present disclosure, vacuum vapor deposition may be used to manufacture the limiting layer, and Ni, Cr, Al, etc. may be used as the anti-etching layer. Preferably, the same material as the flexible separation layer can be used as the anti-etching layer, so that the anti-etching layer and the flexible separation layer can be removed together when the electrode is used. The metal anti-etching layer can be manufactured by the method for manufacturing the metal film described above.

Figure 4:
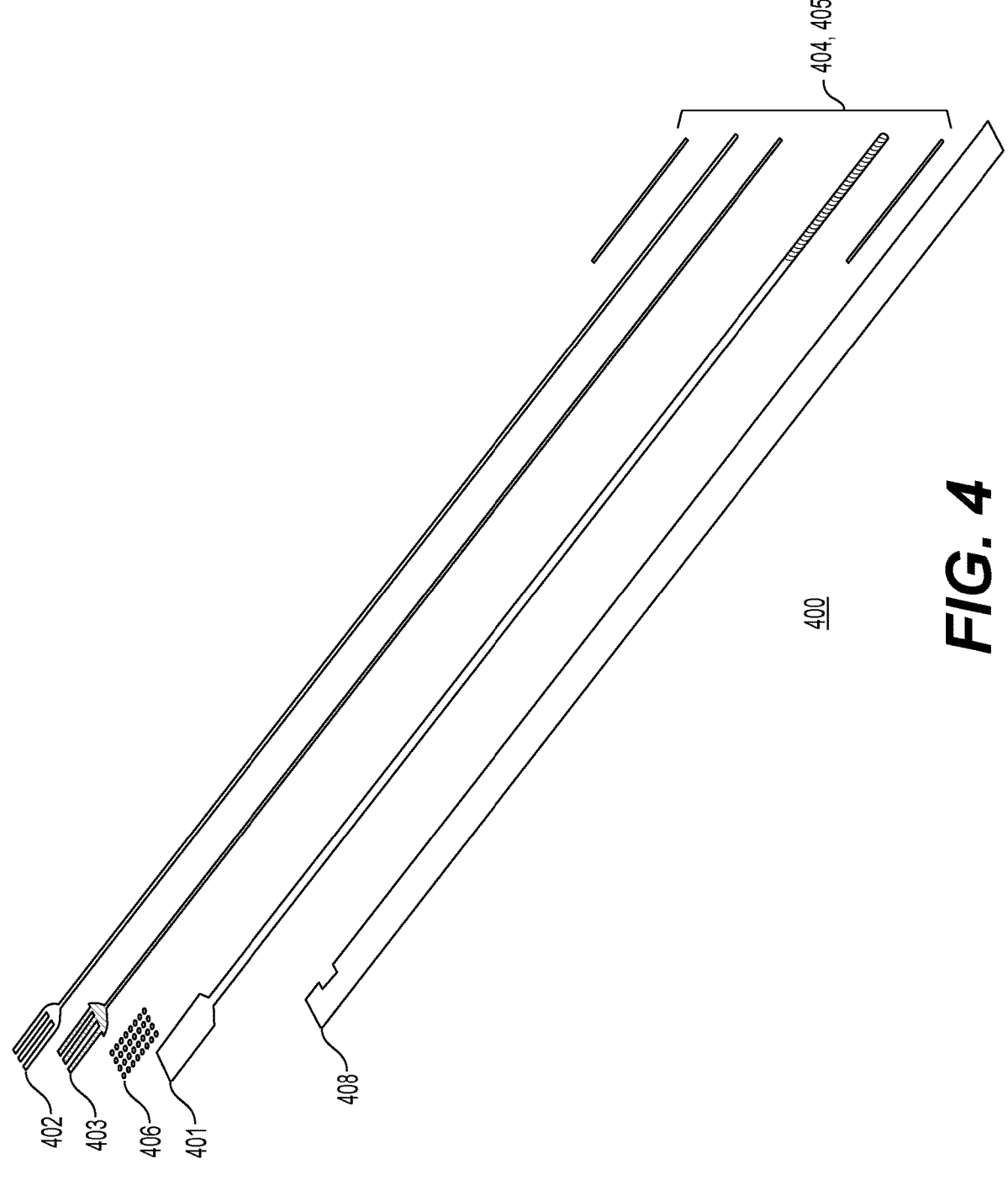
FIG. 4 illustrates an exploded view of at least a portion of a flexible electrode according to an embodiment of the present disclosure.

FIG. 4 illustrates an exploded view of at least a portion of a flexible electrode 400 according to an embodiment of the present disclosure. As shown in FIG. 4, the flexible electrode 400 may comprise a bottom insulating layer 401, a top insulating layer 402, a wire layer 403, a top electrode site layer 404, a bottom electrode site layer 405, a back end site layer 406, a flexible separation layer 408, and the like. Unlike the case in which the contours of the top insulating layer 102 and the bottom insulating layer 101 of the electrode wire shown in FIG. 1 are correspondingly the same, as best shown in FIG. 4, the contour of the bottom insulating layer 401 in the flexible electrode 400 can be different from the contour of the top insulating layer 402 and surround the contour of the top insulating layer 402.

Figure 5:
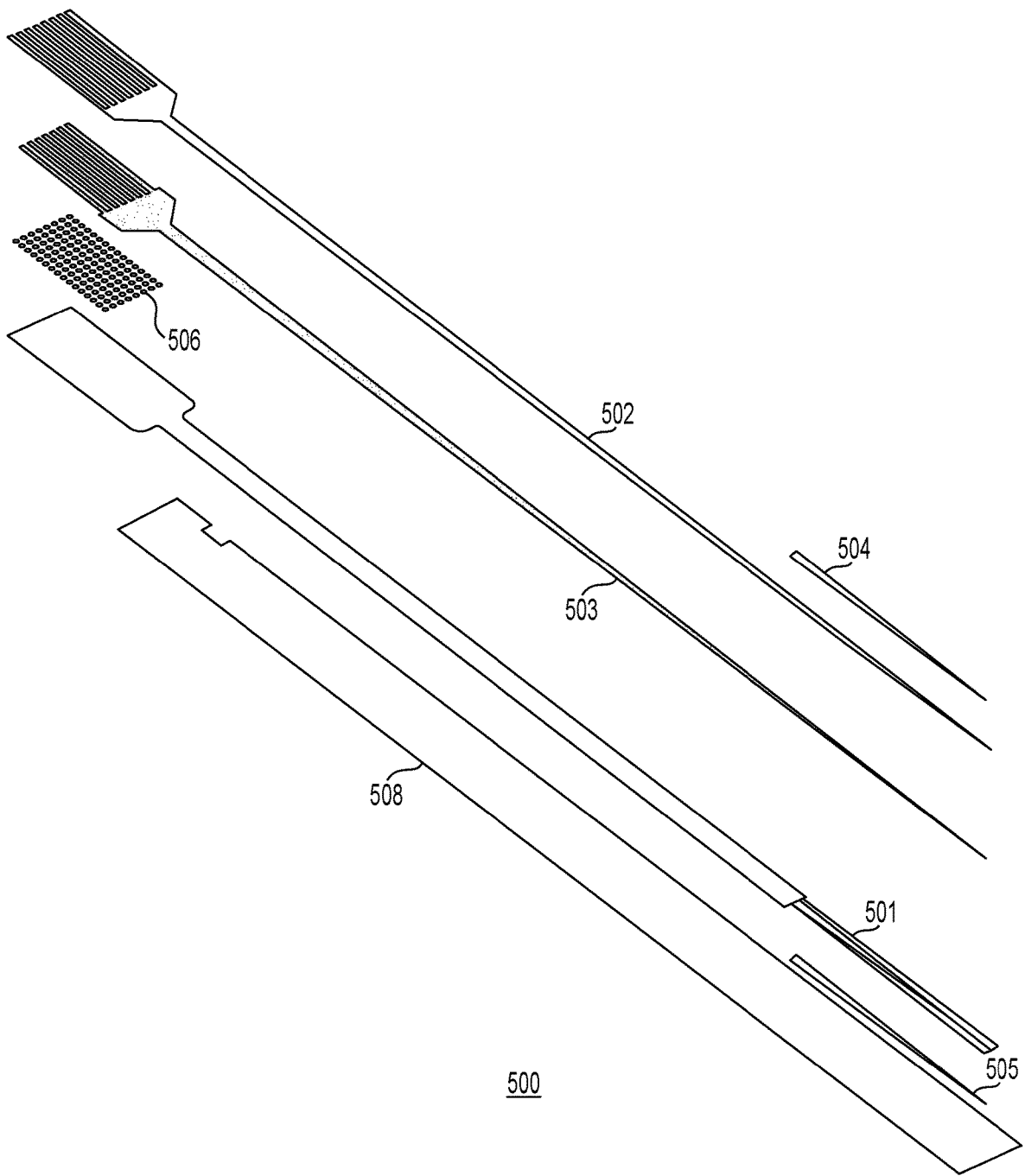
FIG. 5 illustrates an exploded view of at least a portion of a flexible electrode according to an embodiment of the present disclosure.

FIG. 5 illustrates an exploded view of at least a portion of a flexible electrode 500 according to an embodiment of the present disclosure. As shown in FIG. 5, the flexible electrode 500 may comprise a bottom insulating layer 501, a top insulating layer 502, a wire layer 503, a top electrode site layer 504, a bottom electrode site layer 505, a back end site layer 506, a flexible separation layer 508, and the like. As shown in FIG. 5, the contour of the bottom insulating layer 501 may surround the contour of the top insulating layer 502. In addition, unlike the top electrode site layer 404 and the bottom electrode site layer 405 in the single electrode wire shown in FIG. 4, which each comprise only one column of electrode sites, the top electrode site layer 504 and the bottom electrode site layer 505 in the single electrode wire in FIG. 5 comprise two columns of electrode sites, and the bottom insulating layer 501, the top insulating layer 502, the wire layer 503, etc. also change accordingly. It should be understood that the arrangement of electrode sites in the flexible electrode of the present disclosure is not limited thereto, but can be set as required, and the arrangement of other layers in the flexible electrode can be adjusted accordingly.

Figure 6:
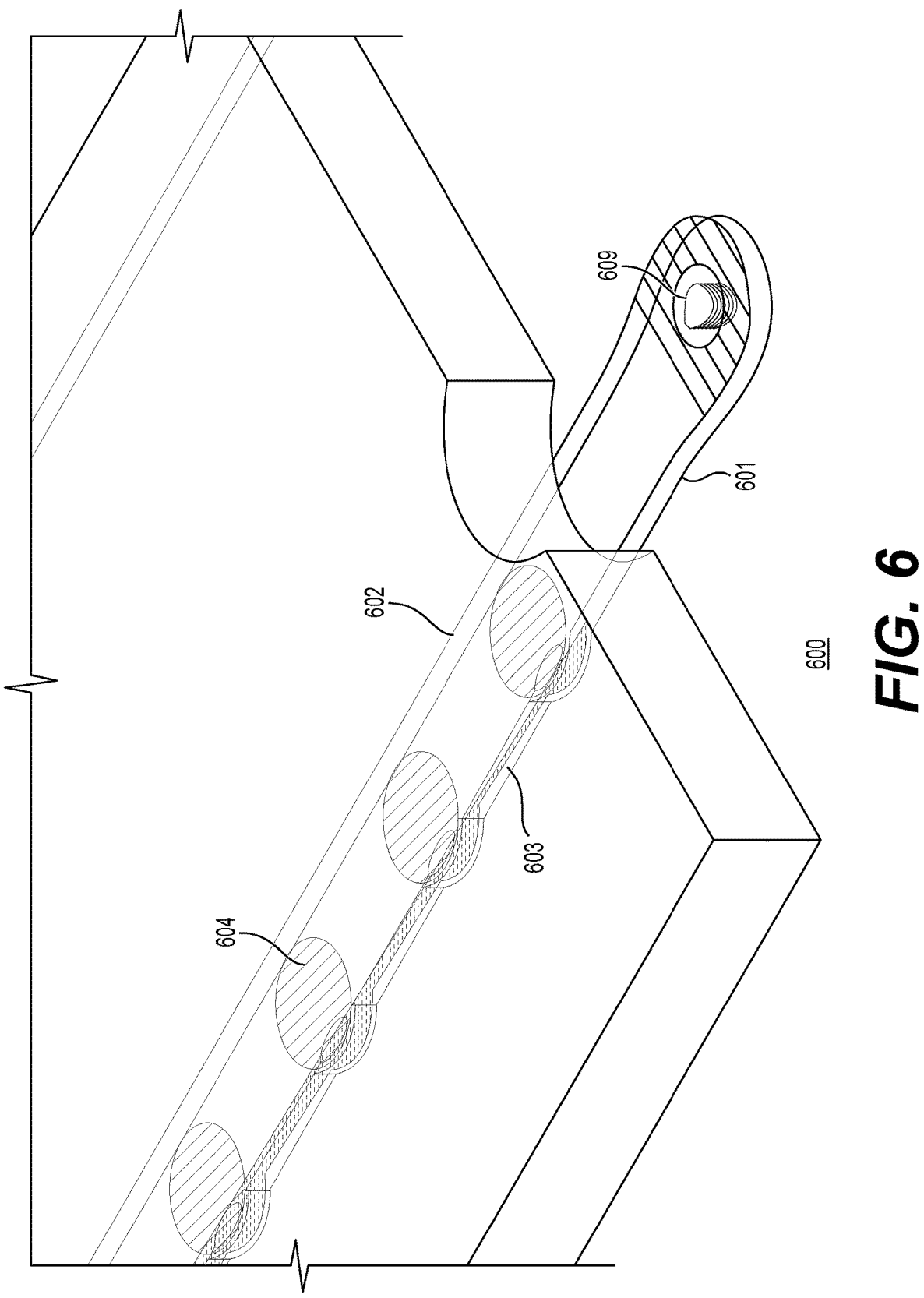
FIG. 6 illustrates an enlarged exploded view of at least a portion of a flexible electrode according to an embodiment of the present disclosure.

FIG. 6 illustrates an enlarged exploded view of at least a portion of a flexible electrode 600 according to an embodiment of the present disclosure. As shown in FIG. 6, the flexible electrode wire 600 may comprise a bottom insulating layer 601, a top insulating layer 602, a wire layer 603, a top electrode site layer 604, a mounting hole 609, and the like. As shown in FIG. 6, the mounting hole 609 may be a hole on the electrode wire for electrode implantation, and the electrode implantation device may be attached to the electrode wire through the mounting hole 609 for implantation. In an embodiment according to the present disclosure, the mounting hole 609 can be a through hole located at an end of the electrode wire away from the back end portion. The electrode implantation device can remove the electrode wire from the substrate through the mounting hole and drive the electrode wire through the mounting hole, thereby guiding the electrode wire to complete the implantation process. In addition, when the flexible electrode comprises a limiting layer, the position of each electrode wire is relatively fixed due to the limiting layer. Therefore, by matching the mounting hole with the limiting layer, automatic implantation of the electrode wire can be realized by using the electrode implantation device advantageously.

Figure 7:
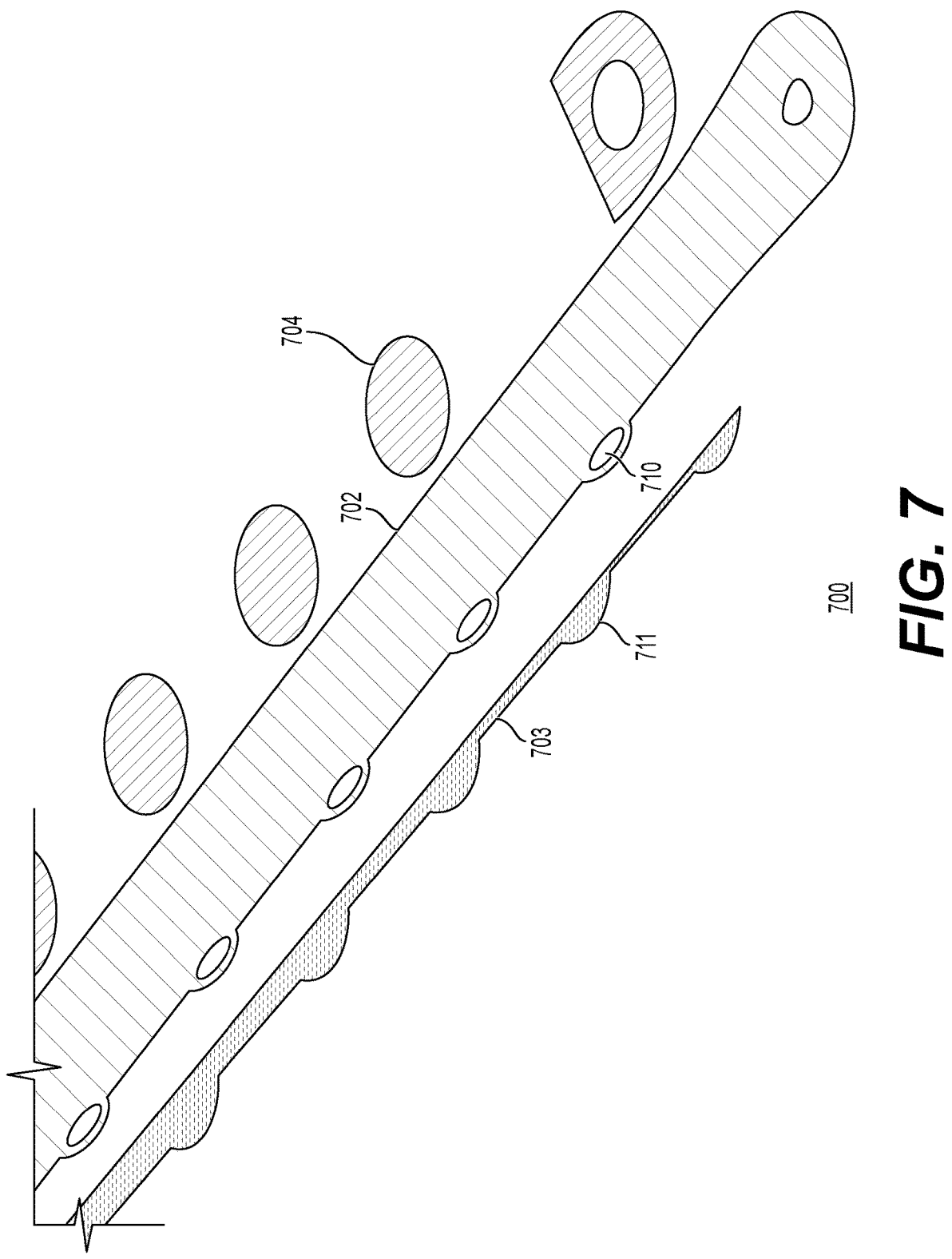
FIG. 7 illustrates an enlarged exploded view of at least a portion of a flexible electrode according to an embodiment of the present disclosure.

FIG. 7 illustrates an enlarged exploded view of at least a portion of a flexible electrode 700 according to an embodiment of the present disclosure. As shown in FIG. 7, the flexible electrode wire 700 may comprise a top insulating layer 702, a wire layer 703, a top electrode site layer 704, and the like. As best shown in FIG. 7, the top insulating layer 702 of the electrode wire 700 can, at positions corresponding to electrode sites in the top electrode site layer 704, have a contour corresponding to at least a portion of the shape of the electrode sites, and the contour surrounds the through holes 710 in the top insulating layer 702 corresponding to the electrode sites. In addition, as best shown in FIG. 7, the wire in the wire layer 703 can, at a position corresponding to a corresponding electrode site to which the wire is electrically coupled, have a contour corresponding to at least a portion of the shape of the corresponding electrode site, such as the arcuate portion 711 of the wire in FIG. 7. Advantageously, the contour of the arcuate portion 711 may surround the contour of the corresponding through hole 710 in the insulating layer 702.

The advantages of the flexible electrode and the manufacturing method therefor according to the present disclosure may include: the insulating layer has excellent biocompatibility while ensuring the strength and flexibility of the electrode, and can achieve long-term implantation; the flexible setting of the electrode site, the multi-wire layer and the multi-wire design of each layer can realize the accurate and high-density collection and application of electrical signals; the use of mounting holes, limiting layers and other designs can realize the automatic implantation of electrodes; it is manufactured using MEMS technology, has a film form of stacked layers, has good electrical, chemical and mechanical properties, the two-dimensional shape and size of each layer can be freely designed, and the integration level can be further improved with the development of photolithography technology. Compared with existing invasive electrode technologies, the flexible electrode according to the present disclosure can achieve long-term stable and high-throughput signal interaction while significantly reducing damage to biological tissues.

Figure 8:
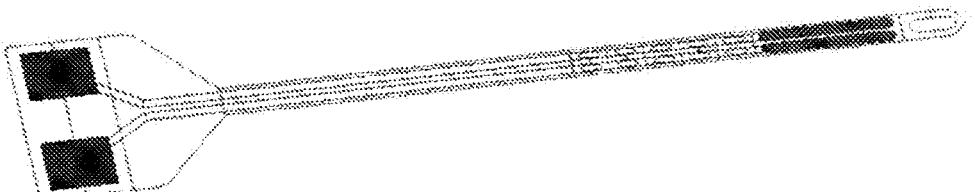
FIG. 8 illustrates a schematic diagram of at least a portion of a flexible electrode according to an embodiment of the present disclosure.
Figure 9:
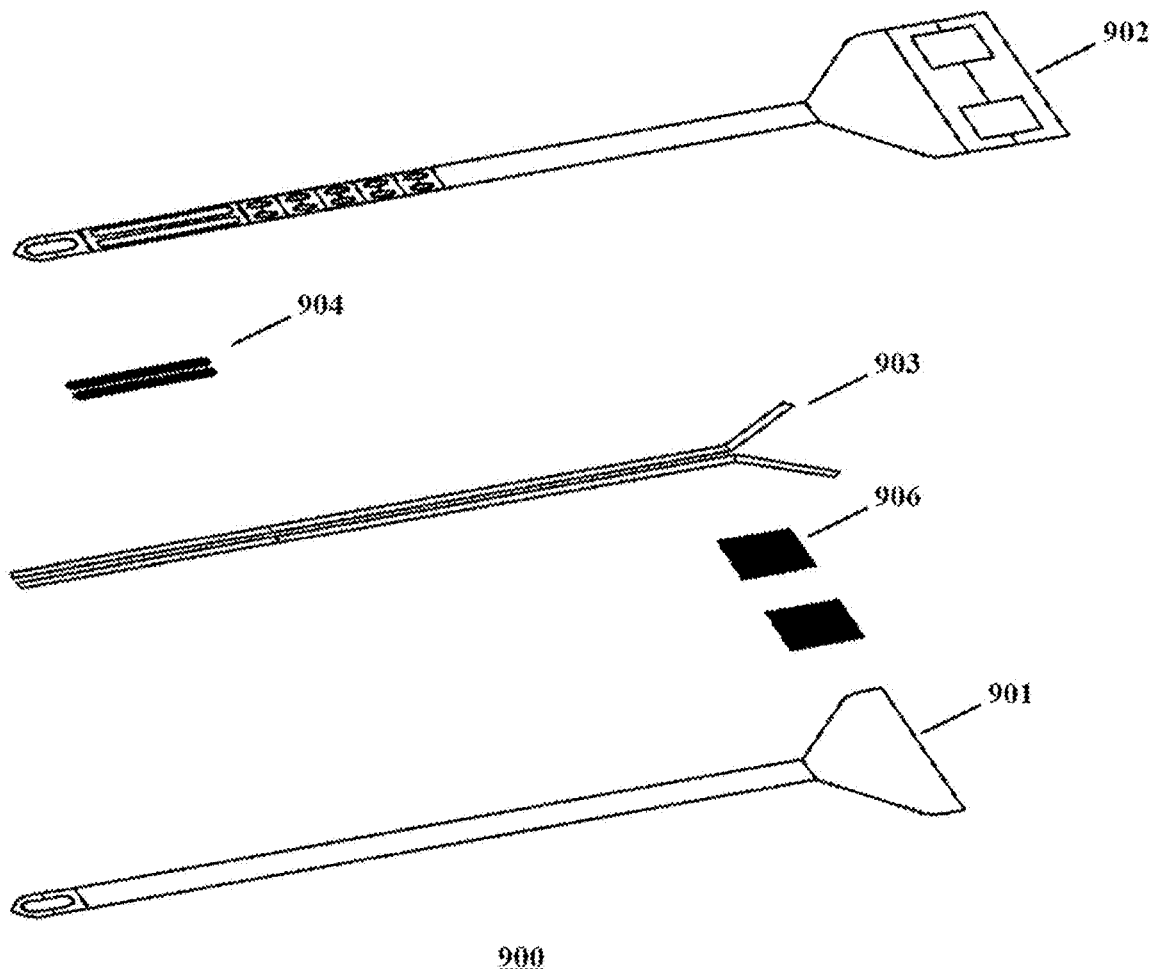
FIG. 9 shows an exploded view of at least a portion of the flexible electrode shown in FIG. 8.

FIGS. 8 and 9 illustrate at least a portion of another flexible electrode according to the present disclosure. The electrodes shown in FIGS. 8 and 9 can be combined with meridian acupoints to serve as acupuncture acupoint electrical stimulating electrodes, which feature flexibility, multi-channel, multi-stimulating contacts, acute or long-term stimulation, and biodegradability. As shown in FIG. 9, the flexible electrode 900 may comprise a bottom insulating layer 901, a top insulating layer 902, a wire layer 903, a top electrode site layer 904, a back end site layer 906, and the like. In addition, although not shown in the figure, the flexible electrode 900 may also comprise other layers described above, such as a flexible separation layer, an additional electrode site layer, an additional wire layer, an additional insulation layer. Asynchronous acupuncture electrodes with different numbers of layers, different numbers of acupuncture contacts, different sizes and shapes, and contact distributions can be designed according to different needs. Specifically, for example, the sites and corresponding wires can asynchronously apply stimulation to the acupoint as needed. In order to achieve biodegradability, the wire layer 903 can be made of degradable metal materials such as Mg and Mo, or conductive metal materials such as Au, Pt, and Ir. The thickness of the wire layer 903 can be 5 nm to 200 μm. When the wire layer 903 comprises a plurality of layers, the thickness of the adhesive layer can be 1 nm to 50 nm, and the thickness of the conductive layer can be 5 nm to 2 μm.

The cross-sectional area of the top electrode site layer can be 0.01 mm$^2$ to 1 mm$^2$. In order to achieve biodegradability, the top insulating layer 902 can be made of medical polymer biodegradable materials such as polylactic acid (PLA), poly (lactic-co-glycolic acid) (PLGA), or SU8 photoresist, PI, PDMS, silica gel, parylene. The thickness of the insulating layer can be 0.5 μm to 3 mm. The bottom insulating layer 901 can play a supporting role, and can be made of an insulating material that is the same as or different from that of the top insulating layer. Medical polymer biodegradable materials can be decomposed in the body, and the decomposition products can be absorbed, metabolized, and eventually excreted from the body. In application, the degradation rate and absorbability of medical polymer biodegradable materials can be adjusted according to different needs by chemically modifying the materials, using composite materials and selecting materials with appropriate degradation rates to adjust the degradation rate of the materials and the way they interact with the body. By implanting degradable flexible acupuncture electrical stimulating electrodes into acupoint tissues, a long-term stimulation effect on the acupoints can be achieved, thus realizing a long-term acupuncture mode. The application of medical polymer biodegradable materials realizes the controllability of the stimulation time and intensity of acupoint tissues by implanted materials, which is conducive to promoting the standardization and regularization of acupuncture medical research and clinical treatment. At the same time, it avoids the defects of traditional acupoint catgut embedding, such as large trauma, susceptibility to infection, immune rejection, and formation of subcutaneous nodules, and has important application value in various chronic diseases in clinical practice.

In the present disclosure, the flexible electrode may be a multi-channel electrode compatible with magnetic resonance imaging (MRI). In order to achieve good MRI compatibility, specifically, the insulating layer can be made of a high molecular polymer material with a lower Young's modulus and higher biocompatibility, such as PI, SU8, silicone rubber. The wires in the wire layer may be made of non-ferromagnetic metal materials with good biocompatibility (such as platinum-iridium alloy, tungsten, gold, titanium alloy) and non-metal materials (such as graphite, carbon nanotubes). Preferably, the width of the wire is 100 nm to 2 μm; the line spacing of the wire is 100 nm to 1.5 μm, which can be adjusted according to the number of channels of the electrode; the wire layer and the electrode site layer can be combined into the same layer or belong to different layers, that is, the wire and the electrode site can be located in the same layer or different layers. The high-density electrode sites in the electrode site layer may be arranged in such a way that the time-varying magnetic field induces a minimum current. Preferably, the size of the electrode sites is 1 μm to 100 μm; the electrode site arrangement density is 25 to 30 electrode sites per micrometer; and the shape of the electrode sites is circular or elliptical. The back end circuit of the flexible electrode can be MRI-compatible, connected to the non-ferromagnetic metal back end through an ultra-flexible PCB adapter board. Preferably, the metal material for connecting the PCB and the back end may be copper (Cu), silver (Ag), Au, etc.

This MRI-compatible flexible electrode enables the simultaneous acquisition of high-throughput, high-quality, long-term stable electrophysiological signals and magnetic resonance imaging signals on the surface and inside of central or peripheral nerve tissues. Specifically, micro-nano processing technology is used to achieve the high-density and microsize arrangement of electrode sites that is close to cellular size; by using metals that are not ferromagnetic and have good biocompatibility, the electrode has good magnetic resonance imaging compatibility, thereby achieving the safety of imaging in magnetic resonance imaging scenarios; by using insulating layer materials with a small Young's modulus, including PI, SU8, etc., the flexibility of the electrode is greatly increased, so that the electrode has a bending force of the order of intercellular interaction force, thereby achieving excellent biocompatibility of the electrode; the sandwich structure of the electrode with a wire layer sandwiched between the two insulating layers makes it ultra-thin of the order of several microns, and the significant reduction in the size of the electrode reduces the use of ferromagnetic metal, indirectly improving the problem of magnetic susceptibility mismatch between the electrode material and the biological tissue, and greatly weakening the artifacts caused by the electrode in MRI; at the same time, the multi-density electrode site size close to cellular size enables the electrode to have high-throughput, high-quality, and stable physiological signal recording capabilities.

This flexible electrode can not only be used to record physiological signals, but also to regulate physiological signals of tissues, such as electrically stimulating nerve or muscle tissues, especially electrically stimulating tissues with implanted electrodes in magnetic resonance imaging scenarios. Electrical stimulation in a magnetic resonance imaging scenario combined with an electrophysiological recording system can synchronously or asynchronously observe the dynamic changes of electrophysiological and metabolic signals in response to stimulation, which is of great significance to basic research and clinical disease diagnosis and treatment. In addition, the flexible electrode can also be used for recording and regulating brain electrophysiological signals (such as, attached to the surface of the brain, inside the brain, or both), recording and regulating spinal cord electrophysiological signals (such as, attached to the surface of the spinal cord, inside the spinal cord, or both), recording and regulating peripheral electrophysiological signals (such as, attached to the surface, inside, or both of peripheral nerves such as the sciatic nerve and vagus nerve), recording and regulating muscle electrophysiological signals (such as, implanted inside muscles) in magnetic resonance imaging scenarios, etc. This flexible electrode can be used in 9T magnetic resonance imaging scenarios and successfully record signals, and has achieved long-term stable implantation for more than 2 months.

In the present disclosure, the flexible electrode may be a stimulating electrode for finely stimulating biological tissues (such as peripheral neurons) to obtain the response under stimulation parameters. The stimulating electrode can be an important part of the deep brain electrical stimulating system. In addition to the stimulating electrode, the system can also comprise a pulse generator, an extension wire and other parts. The stimulating electrode can be implanted in the brain, the pulse generator can be implanted subcutaneously in the chest, and the extension wire can connect the electrical stimulating electrode and the pulse generator subcutaneously.

The stimulating electrode according to the present disclosure may comprise an implantation segment (i.e., the electrode wire described above) and a connection segment with a back end circuit (i.e., the back end portion described above) along the length direction, and the width of the implantation segment may be smaller than the width of the connection segment. Similar to the structure of the flexible electrode described above, the stimulating electrode may comprise a bottom insulating layer, a wire layer, a top insulating layer, an electrode site layer and a back end site layer. The electrode site layer, the back end site layer, and the wire layer can be combined into the same layer, or belong to different layers. The insulating layer of the stimulating electrode may be made of a flexible polymer material having biocompatibility, such as any one of polyimide, SU 8 or parylene, or a combination of at least two thereof. Furthermore, the materials of the substrate insulating layer and the top insulating layer can be the same or different. The wire layer of the stimulating electrode may comprise one or more wires for connecting electrode sites in the electrode site layer to the back end circuit in the back end site layer. The electrode site layer of the stimulating electrode may comprise at least two electrode sites having a shape without sharp tips to avoid point discharge. In an embodiment according to the present disclosure, the electrode sites may be located in the wire layer, i.e., the electrode site layer is located in the same layer as the wire layer, and the electrode sites are exposed by means of through holes in the insulating layer. In an embodiment according to the present disclosure, the thickness of the wire layer may be 5 nm to 3000 nm. In an embodiment according to the present disclosure, the electrode sites may be arranged linearly on the implantation segment along the length direction of the electrode. The number of electrode sites may be 2 to 1000; the distance between electrode sites may be 0.01 mm to 25 mm. In addition, the surface of the electrode site may be modified, and the material for modification may include conductive polymers and/or conductive metal particles, and the modification method may include electrodeposition and/or self-assembly. The conductive polymer may include poly(ethylenedioxythiophene), poly(p-styrene sulfonic acid) and/or polypyrrole, etc.; the material of the conductive metal particles may include iridium, iridium oxide, platinum or platinum-iridium alloy, etc. The implantation segment of the stimulating electrode may further comprise a positioning implant ring (i.e., the mounting hole mentioned above), which is located at one end of the implantation segment away from the connection segment. The positioning implant ring may be provided with a positioning hole on the insulating layer where it is located. In addition, the stimulating electrode may further comprise a switching structure for connecting the stimulating electrode to different adapter terminals. Preferably, the switching structure may be cylindrical and located in the connection segment, the two insulating layers cover the outer circumference of the switching structure, and one side of the bottom insulating layer is attached to the switching structure. Preferably, the material of the switching structure may include a flexible polymer material with biocompatibility, such as any one of silicone rubber, polyurethane or polydimethylsiloxane, or a combination of at least two thereof. In an embodiment of the present disclosure, the materials of the electrode sites, wires and positioning implant rings may include any one of platinum, iridium or gold or a combination of at least two thereof; and the materials of the electrode sites, wires and positioning implant rings may be the same or different.

The method for manufacturing such a stimulating electrode may be similar to the manufacturing method for the flexible electrode described above. In addition, when manufacturing the flexible separation layer, magnetron sputtering coating and/or electron beam evaporation processes can be adopted; when manufacturing the bottom insulating layer, additional heating can be performed after spin coating; when manufacturing the top and bottom insulating layers, instead of the etching process described above, an ultraviolet photolithography process can be adopted; when manufacturing the wire layer, the electrode site layer, the back end site layer, etc., electron beam evaporation or thermal evaporation can be adopted; when separating the flexible electrode from the substrate, in addition to removing the flexible separation layer, a scribing process can also be adopted.

The stimulating electrode can achieve fine stimulation. For example, it can use two-photon calcium imaging technology to simultaneously observe the electrode and the surrounding neurons in the field of view, and can respond to neurons as low as 50 μm around the electrode. It adopts high-molecular polymer substrate materials and reduces the electrode size to the cellular level through micro-nano processing, thereby constructing a neural interface that can achieve long-term stable recording and stimulation without glial scars.

The words "front", "back", "top", "bottom", "above", "under" and the like in the specification and claims, if present, are used for descriptive purposes and not necessarily for describing unaltered relative positions. It is to be understood that the terms so used are interchangeable under appropriate circumstances such that the embodiments of the present disclosure described herein are, for example, capable of operation in other orientations than those illustrated or otherwise described herein.

As used herein, the word "exemplary" means "serving as an example, instance, or illustration" rather than as a "model" to be exactly copied. Any implementation described herein as exemplary is not necessarily to be construed as preferred or advantageous over other implementations. Furthermore, the present disclosure is not bound by any expressed or implied theory presented in the preceding Field of the Invention, Background of the Invention, Summary of the Invention or Detailed Description of the Invention.

As used herein, the word "substantially" is meant to include any minor variations caused by design or manufacturing defects, device or component tolerances, environmental influences, and/or other factors. The word "substantially" also allows for deviations from the perfect or ideal situations due to parasitic effects, noise, and other practical considerations that may be present in actual implementations.

The terms "first", "second" and the like may be used herein for reference purposes only and thus are not intended to be limiting. For example, the terms "first," "second," and other such numerical words when referring to structures or elements do not imply a sequence or order unless clearly indicated by the context.

It should also be understood that when the word "include/comprise" is used herein, it indicates the presence of the specified features, integers, steps, operations, units and/or components, but does not exclude the presence or addition of one or more other features, integers, steps, operations, units and/or components and/or combinations thereof.

As used herein, the term "and/or" includes any and all combinations of one or more of the associated listed items. The terms used herein are for the purpose of describing particular embodiments only and are not intended to limit the present disclosure. As used herein, the singular forms "a", "an" and "the" are intended to include the plural forms as well, unless the context clearly indicates otherwise.

Those skilled in the art will appreciate that the boundaries between the above operations are merely illustrative. Multiple operations may be combined into a single operation, a single operation may be distributed among additional operations, and operations may be performed at least partially overlapping in time. Moreover, alternative embodiments may include multiple instances of a particular operation, and the order of operations may be altered in various other embodiments. However, other modifications, variations, and replacements are also possible. The specification and drawings are, accordingly, to be considered as illustrative rather than restrictive.

Although some specific embodiments of the present disclosure have been described in detail through examples, those skilled in the art should understand that the above examples are only for illustration rather than for limiting the scope of the present disclosure. The various embodiments disclosed herein may be combined in any manner without departing from the spirit and scope of the present disclosure. It will also be appreciated by those skilled in the art that various modifications may be made to the embodiments without departing from the scope and spirit of the present disclosure. The scope of the present disclosure is defined by the appended claims.

The invention claimed is:

1. A flexible electrode, comprising:
at least one implantable and flexible electrode wire; and
a continuous limiting layer,
wherein each electrode wire comprises:
    a wire located between a first insulating layer and a second insulating layer, and
    an electrode site, in contact with a biological tissue after implantation of the electrode wire, located on the second insulating layer and electrically coupled to the wire located between the first insulating layer and the second insulating layer by means of a through hole in the second insulating layer,
wherein the continuous limiting layer is located on the at least one electrode wire and is configured to be detachably adhered to the at least one electrode wire, so that the at least one electrode wire is kept in a fixed arrangement during the implantation process, and
wherein the continuous limiting layer comprises at least one through hole that extends through a thickness of the continuous limiting layer, the at least one through hole being at a position corresponding to a respective electrode site on the at least one electrode wire, a contour of each of the at least one through hole being surrounded by a contour of the respective electrode site.

2. The flexible electrode according to claim 1, wherein:
the wire in each electrode wire comprises a plurality of wires located in a wire layer of the flexible electrode and separated from each other, and
the electrode site in each electrode wire comprises a plurality of electrode sites each electrically coupled to one of the plurality of wires through a corresponding through hole in the second insulating layer.

3. The flexible electrode according to claim 2, wherein:
the flexible electrode comprises a plurality of wire layers, the plurality of wire layers are separated by additional insulating layers, and each wire layer comprises a plurality of wires separated from each other.

4. The flexible electrode according to claim 1, further comprising a back end portion, each electrode wire extending from the back end portion, wherein the back end portion comprises back end sites, each of which is electrically coupled to a respective wire and a back end circuit by means of a through hole in the first insulating layer and/or the second insulating layer, thereby achieving bidirectional signal transmission between each electrode site and the back end circuit.

5. The flexible electrode according to claim 4, wherein each back end site is obtained by stacking a plurality of layers, and the plurality of layers include an adhesive layer, a flux layer, a conductive layer, and a protective layer.

6. The flexible electrode according to claim 4, wherein each back end site comprises a metal film having three layers, the three layers comprising a first layer, closest to the respective wire, comprising titanium, titanium nitride, chromium, tantalum or tantalum nitride, a second layer comprising nickel, platinum or palladium, and a third layer, furthest from the respective wire, comprising any one of gold, platinum, iridium, tungsten, magnesium, molybdenum, platinum-iridium alloy, titanium alloy, graphite, carbon nanotubes, PEDOT or a combination thereof.

7. The flexible electrode according to claim 4, wherein the flexible electrode is connected to the back end circuit via a printed circuit board or a flexible circuit board through the back end sites, or wherein the flexible electrode is configured to be integrated in a reserved space on a pre-tapeout wafer of a chip serving as the back end circuit, so that the flexible electrode and the chip can be processed jointly or separately.

8. The flexible electrode according to claim 1,
wherein the material of the limiting layer is any one of parylene, polydimethylsiloxane, UV film, electronic grade tape, and plastic film with heat shrinkage properties, or a combination thereof.

9. The flexible electrode according to claim 1, wherein the material of the first insulating layer and the second insulating layer is any one of polyimide, polydimethylsiloxane, parylene, epoxy resin, polyamideimide, polylactic acid, poly(lactic-co-glycolic acid), SU8 photoresist, silica gel, silicone rubber or a combination thereof.

10. The flexible electrode according to claim 1, wherein the second insulating layer of each electrode wire has a contour corresponding to at least a portion of the shape of electrode sites at positions corresponding to the electrode sites, and the contour surrounds the through holes corresponding to the electrode sites.

11. The flexible electrode according to claim 10, wherein the first insulating layer of each electrode wire has a contour that is the same as or surrounds the contour of the second insulating layer.

12. The flexible electrode according to claim 1, wherein the material of the wire is any one of gold, platinum, iridium, tungsten, magnesium, molybdenum, platinum-iridium alloy, titanium alloy, graphite, carbon nanotubes, PEDOT or a combination thereof.

13. The flexible electrode according to claim 1, wherein the wire is obtained by stacking a plurality of layers, and the material of the layer in contact with the first insulating layer or the second insulating layer among the plurality of layers is a material capable of enhancing adhesion between the wire and the first insulating layer or the second insulating layer.

14. The flexible electrode according to claim 13, wherein the wire is a metal film obtained by stacking three layers, wherein the materials of the first layer and the second layer in contact with the first insulating layer and the second insulating layer respectively are titanium, titanium nitride, chromium, tantalum or tantalum nitride, and the material of the third layer located between the first layer and the second layer is any one of gold, platinum, iridium, tungsten, magnesium, molybdenum, platinum-iridium alloy, titanium alloy, graphite, carbon nanotubes, PEDOT or a combination thereof.

15. The flexible electrode according to claim 1, wherein the wire, at a position corresponding to a corresponding electrode site to which the wire is electrically coupled, has a contour corresponding to at least a portion of the shape of the corresponding electrode site.

16. The flexible electrode according to claim 1, wherein the electrode site is obtained by stacking a plurality of layers, wherein the material of the first layer close to the wire among the plurality of layers is a material capable of enhancing adhesion between the electrode site and the wire.

17. The flexible electrode according to claim 16, wherein the electrode site is a metal film obtained by stacking two layers, wherein the material of the first layer close to the wire is titanium, titanium nitride, chromium, tantalum or tantalum nitride, and the material of the second layer exposed to the outside is any one of gold, platinum, iridium, tungsten, magnesium, molybdenum, platinum-iridium alloy, titanium alloy, graphite, carbon nanotubes, PEDOT or a combination thereof.

18. The flexible electrode according to claim 1, wherein the shape, size and spacing of the electrode sites are selected according to the conditions of the biological tissue area to be recorded.

19. The flexible electrode according to claim 1, wherein the surface of the electrode site in contact with the biological tissue has a surface modification layer to improve the electrochemical properties of the electrode site.

20. The flexible electrode according to claim 19, wherein the surface is modified by any one or more of a conductive polymer and conductive metal particles, the conductive polymer includes poly(ethylenedioxythiophene), poly(p-styrene sulfonic acid), and polypyrrole, and the material of the conductive metal particles includes iridium, iridium oxide, platinum, and platinum-iridium alloy.

21. The flexible electrode according to claim 1, wherein the electrode wire further comprises an additional electrode site that is in contact with a biological tissue after implantation of the at least one electrode wire, the additional electrode site being located under the first insulating layer and electrically coupled to the wire by means of a through hole in the first insulating layer.

22. The flexible electrode according to claim 21, wherein the additional electrode site and the electrode site are at opposite positions on two sides of the flexible electrode, respectively, and the additional electrode site and the electrode site are electrically coupled to the same wire.

23. The flexible electrode according to claim 1, wherein each electrode wire has a mounting hole, and an electrode implantation device is attached to the electrode wire through the mounting hole for implantation.

24. The flexible electrode according to claim 1, further comprising a flexible separation layer, wherein the flexible separation layer is capable of being removed by a specific substance to separate portions of the flexible electrode while avoiding damage to the flexible electrode.

25. The flexible electrode according to claim 24, wherein the electrode site of the flexible electrode is a metal film obtained by stacking three layers, and the outermost layer of the three layers in contact with the flexible separation layer is made of the same material as the flexible separation layer, and is used to separate the electrode site from the limiting layer of the flexible electrode by removing the flexible separation layer.

26. The flexible electrode according to claim 1, wherein the flexible electrode has magnetic resonance imaging compatibility, or
wherein the flexible electrode is a degradable acupuncture electrode, used for acute stimulation or long-term stimulation in combination with meridian acupoints, and the shape, size and spacing of the electrode sites of the degradable acupuncture electrode are selected according to needs.

27. The flexible electrode according to claim 26, wherein the electrode site of the degradable acupuncture electrode is located proximate the at least one electrode wire and is exposed by means of a through hole in the first insulating layer and/or the second insulating layer.

28. The flexible electrode according to claim 1, wherein the flexible electrode is a stimulating electrode, the shape of the electrode site of the stimulating electrode has no tip, the surface of the electrode site of the stimulating electrode is modified, the material for modification includes at least one of a conductive polymer and conductive metal particles, the modification method includes at least one of electrodeposition and self-assembly, the conductive polymer includes one or more of poly(dioxyethylthiophene), poly(p-styrene sulfonic acid) or polypyrrole, the material of the conductive metal particles includes one or more of iridium, iridium oxide, platinum or platinum-iridium alloy, and the thickness of the wire layer of the stimulating electrode is 5 nm to 3000 nm.

29. The flexible electrode according to claim 28, wherein the electrode site of the stimulating electrode is located proximate the at least one electrode wire and is exposed by means of a through hole in the first insulating layer and/or the second insulating layer.

30. The flexible electrode according to claim 1, wherein the at least one electrode wire comprises two or more electrode wires.

* * * * *